United States Patent [19]

Raccah

[11] 4,291,975
[45] Sep. 29, 1981

[54] APPARATUS FOR DETERMINING THE COLOR CHARACTERISTICS OF A GEM

[75] Inventor: Paul M. Raccah, Chicago, Ill.

[73] Assignee: Scientific Gem Identification, Inc., Los Angeles, Calif.

[21] Appl. No.: 113,777

[22] Filed: Jan. 21, 1980

Related U.S. Application Data

[63] Continuation-in-part of Ser. No. 81,363, Oct. 3, 1979, abandoned, which is a continuation of Ser. No. 916,120, Jun. 16, 1978, abandoned.

[51] Int. Cl.³ .............................................. G01N 21/27
[52] U.S. Cl. ...................................... 356/30; 356/319
[58] Field of Search ................................... 356/30, 319

[56] References Cited

U.S. PATENT DOCUMENTS

| | | | |
|---|---|---|---|
| 2,960,909 | 11/1960 | Shipley, Jr. | 356/30 |
| 3,794,424 | 2/1974 | Eickhorst et al. | 356/30 |
| 3,867,032 | 2/1975 | Bruck | 356/30 |
| 3,989,379 | 11/1976 | Eickhorst | 356/30 |
| 4,029,419 | 6/1977 | Schumann et al. | 356/418 |
| 4,125,329 | 11/1978 | French et al. | 356/418 |

*Primary Examiner*—F. L. Evans

*Attorney, Agent, or Firm*—Fulwider, Patton, Rieber, Lee & Utecht

[57] ABSTRACT

Method and apparatus for measuring the spectral transmission characteristics of gems, particularly diamonds. Polychromatic light from a light source is transmitted through a diamond to be analyzed, after which the transmitted light beam is separated into a plurality of separate wavelength bands and the intensity of light in the successive bands is measured by a first linear array of photodiodes. Simultaneously, a reference beam of light from the light source is separated into a plurality of corresponding wavelength bands, and the intensity of light in the successive bands are measured by a second linear array of photodiodes. The two measurements produced by each pair of corresponding photodiodes are then compared with each other, to provide a plurality of measurements indicative of the transmission characteristics of the diamond for the plurality of wavelength bands. The transmission measurements for prescribed groupings of wavelength bands are then averaged and compared with each other in a prescribed fashion, to accurately grade the diamond according to conventional grading standards.

27 Claims, 4 Drawing Figures

Fig. 4

APPARATUS FOR DETERMINING THE COLOR CHARACTERISTICS OF A GEM

BACKGROUND OF THE INVENTION

This is a continuation-in-part of application Ser. No. 081,363, filed Oct. 3, 1979 and now abandoned, which in turn is a continuation of application Ser. No. 916,120, filed June 16, 1978 and now abandoned.

This invention relates generally to devices for determining the quality of gems and, more particularly, to an optical apparatus and methods for determining the color characteristics of gems, especially diamonds.

Determining the color characteristics of a diamond has traditionally been accomplished by a visual comparison of the diamond to other diamonds of known quality, under prescribed lighting conditions. Accurate visual comparisons of this type require substantial training and experience; however, even then, these comparisons are highly subjective in nature.

Recently, a number of devices and related methods have been developed for more objectively measuring the color characteristics of gems, and particularly diamonds. Such devices have typically included a light source for directing polychromatic light at the diamond, which transmits the light in accordance with its color characteristics, and the intensity of the transmitted light in a number of separate wavelength bands is measured by interposing a plurality of optical band-pass filters between the light source and a phototransducer, in a sequential fashion. The various measurements of light intensity are then compared with each other to determine the color characteristics of the diamond. Other devices utilize optical prisms to separate the transmitted light into its various wavelength components, and the intensity of each wavelength component is measured by a separate phototransducer.

Although these prior devices have functioned to provide measurements corresponding generally to those determined visually by skilled observers, the devices have not proven completely satisfactory for a number of reasons, primarily because they have not included means for compensating for non-uniformities in the spectral distribution of the light emitted by the light source and for time variations in that spectral distribution. Also, many of such devices have not compensated for variations in the sensitivities of the phototransducers to the various wavelengths being considered.

Some of these drawbacks have been overcome by improved devices that normalize each light intensity measurement in accordance with the measured intensity, in that particular wavelength band, of the incident light beam prior to transmission through the diamond. However, light intensity measurements of the incident beam and the transmitted beam are normally performed in a sequential fashion, so it does not appear that time variations in the spectral distribution of the light are compensated for.

Another deficiency associated with the aforementioned prior devices arises from their use of light sources that are energized for relatively long periods of time. This can result in excessive heat that can sometimes adversely affect the accuracy of the light intensity measurements.

Although the aforementioned devices function to produce measurements of the spectral transmission characteristics of diamonds, there is not believed to be any prior teaching of accurate and reliable techniques for utilizing these measurements to properly grade the diamonds in accordance with conventional Gemological Institute of America (GIA) grading standards. Specifically, these conventional gradings include color grade, fluorescence, yellow character, brown character, and brilliance.

Prior U.S. Pat. No. 3,794,424 to M. Eickhorst et al discloses on technique for determining the color grade of a diamond, in which the transmission of the diamond is measured first at a wavelength of 415.5 nanometers (nm) and then at a wavelength above 500 nm. This techniques is not believed to be completely satisfactory, however, because it is normally difficult to obtain sufficient power in such narrow wavelength bands to overcome the adverse effects of noise. Also, it appears that the presence of brownness or yellowness in the diamonds being examined might affect the determination of color grade using this technique.

One technique for measuring the yellow character of a diamond is disclosed in prior U.S. Pat. No. 2,960,909 to R. M. Shipley, Jr., which teaches that yellowness is proportional to the transmission of the diamond in the yellow wavelength region divided by the transmission of the diamond in the blue wavelength region. Although this method does provide a measure of yellow character, it is not believed to provide a completely reliable measure under all circumstances.

Particular difficulty has been encountered in the past in devising objective techniques for grading diamonds in accordance with their brown character and fluorescence. Brownness is caused by a relatively high density of impurities, which can cause the diamond to absorb a significant amount of light over a broad range of the visible spectrum, giving the diamond a brownish color that can be detected visually by a skilled observer. Similarly, fluorescence is caused by the presence of a fluorescent impurity, which functions to transform impinging ultra-violet light into light in the visible spectrum, particularly in the blue-violet wavelength range. In diamonds having a relatively high density of impurities, it frequently occurs that some of the impurities are fluorescent. Consequently, many brown diamonds are also fluorescent. The visible light produced by fluorescence in a diamond is normally not visually distinguishable from other visible light transmitted by the diamond. This gives rise to a particularly difficult problem in determining the quality of diamonds. That is, while brown characteristics tend to darken the color of a diamond, fluorescence tends to lighten it, and thus under some lighting conditions, the diamond will appear to be reasonably clear, while under other conditions it may appear to be of lesser quality.

It will be appreciated from the foregoing that there is a definite need for an effective and reliable apparatus for measuring the color characteristics of gems, particularly diamonds, along with methods for use with the apparatus for accurately grading diamonds according to their color grade, yellowness, brownness, fluorescence, and brilliance. Moreover, such grading should desirably correspond to those provided empirically by skilled observers under ideal conditions. The present invention fulfills these needs.

SUMMARY OF THE INVENTION

The present invention is embodied in apparatus and related methods for accurately determining the spectral transmission characteristics of gems, particularly diamonds. The apparatus and methods are further effective in accurately and reliably grading diamonds according to their color grade, yellowness, brownness, fluorescence, and brilliance. The apparatus includes a light source for directing polychromatic light at the gem being examined, which transmits the light in accordance with its inherent color characteristics, and this transmitted light is then directed along a gem channel optical path that includes means for dispersing the light into its component wavelength bands. The light in each band is directed at a separate phototransducer, to produce a plurality of light intensity measurements representative of the spectral distribution of the transmitted light.

In accordance with the invention, the apparatus further includes means for simultaneously directing a reference beam of light from the light source along a reference channel optical path, similar to the gem channel optical path, that includes means for dispersing the light into its component wavelength bands. The light in each wavelength band is then directed at a separate phototransducer, to produce a plurality of light intensity measurements representative of the spectral distribution of the light from the light source. The plurality of measurements of the light transmitted by the gem are then compared with the corresponding measurements of the reference light beam, in a prescribed fashion, to produce a plurality of normalized transmission measures indicative of the spectral transmission characteristics of the gem.

More particularly, the polychromatic light emitted by the light source has a significant intensity over the entire visible wavelength range, i.e. about 400 nm to 700 nm, and over the near ultra-violet range extending from about 350 nm to 400 nm. In measuring the color characteristics of a conventional cut diamond, the diamond is positioned on a diffuser plate such that the polychromatic light enters the diamond through its facets, is reflected internally, and is then transmitted out through the table of the diamond. Simultaneously, a separate portion of the polychromatic light is reflected from a mirror positioned adjacent to the diamond, to produce the reference channel light beam. The gen channel and reference channel light beams are then refracted in a prism and focused onto separate linear arrays of photodiodes.

In accordance with one feature of the invention, the light source comprises a flash lamp that is pulsed for a duration sufficient only to permit the photodiodes in the two arrays to produce substantially stable electrical output signals whereby an excessive build-up of heat from the light source is avoided. The apparatus further includes means for storing a calibration factor for each pair of corresponding photodiodes in the two arrays, whereby the transmission measurements can be appropriately adjusted to correct for differences in the sensitivities of the photodiodes and for differences in the transmission characteristics of the two optical paths.

Thus, in operation, a first portion of the polychromatic light is transmitted through the gem, to produce the gem channel light beam that is directed along the gem channel optical path, where it is separated into a plurality of wavelength bands and focused onto one array of photodiodes. Simultaneously, a second portion of the polychromatic light is reflected by the mirror to produce the reference channel light beam that is directed along the reference channel optical path, where it is separated into a plurality of corresponding wavelength bands and focused onto the other array of photodiodes. Each gem channel measurement is then divided by the corresponding reference channel measurement, to produce a plurality of quotients indicative of the difference in light intensity for each wavelength band. These quotients are then adjusted in accordance with the stored calibration factors for the corresponding photodiode pairs, yielding a plurality of normalized measures indicative of the actual spectral transmission characteristics of the gem being examined.

In accordance with the methods of the present invention, the plurality of normalized transmission measurements are compared to each other in a prescribed fashion to appropriately grade a diamond according to its color grade, fluorescence, brown character, yellow character, and brilliance. Specifically, color grade is determined by comparing the transmission of the diamond in the ultraviolet region with the transmission in a reference region, where the transmission characteristics of most diamonds are substantially the same. In the preferred embodiment, this is accomplished by determining the average value of the normalized transmission measurements corresponding to the wavelength range between about 350 nm and 400 nm, and by then dividing this value by the average value of the normalized measurements for the red-orange wavelength region, extending between about 650 nm and 700 nm.

Further, the yellow character of the diamond being examined is determined by comparing its transmission in the blue-green wavelength region with that in a reference wavelength region such as the red-orange region. Preferably, this is accomplished by determining the average value of the normalized transmission measurements for wavelengths between about 450 nm and 550 nm, and by then dividing this value by the aforementioned average value of measurements for wavelengths between about 650 nm and 700 nm.

In accordance with another aspect of the invention, the brown character of the diamond is determined by comparing the transmission of the diamond in the yellow-orange wavelength region with that in a reference wavelength region such as the red-orange region. In the preferred embodiment, this is accomplished by determining the average value of measurements for wavelengths between about 525 nm and 625 nm, and by then dividing this value by the aforementioned average value for wavelengths between about 650 nm and 700 nm.

In accordance with still another aspect of the present invention, the fluorescence of the diamond is determined by first comparing the transmission characteristics of the diamond in the blue-violet wavelength range to that in a reference wavelength range such as the red-orange range, and by then comparing the results of that comparison to the color grade determination, discussed above. Specifically, the average value of transmission measurements in the wavelengths range of about 400 nm to 500 nm is divided by the aforementioned average value for the wavelength range of 650 nm to 700 nm, and the resultant quotient is then compared to the color grade determination. The amount by which the blue-violet quotient exceeds the ultra-violet quotient (i.e., the color grade) is then indicative of the degree of fluorescence in the diamond.

Finally, in accordance with still another aspect of the invention, a measure of the brilliance of the diamond is obtained by summing together all of the normalized transmission measurements, and by then dividing this sum by a measure of the average diameter of the diamond.

Other aspects and advantages of the present invention will become apparent from the following description of the preferred embodiment, taken in conjunction with the accompanying drawings, which disclose, by way of example, the principles of the invention.

DESCRIPTION OF THE PREFERRED EMBODIMENT

Figure 1:
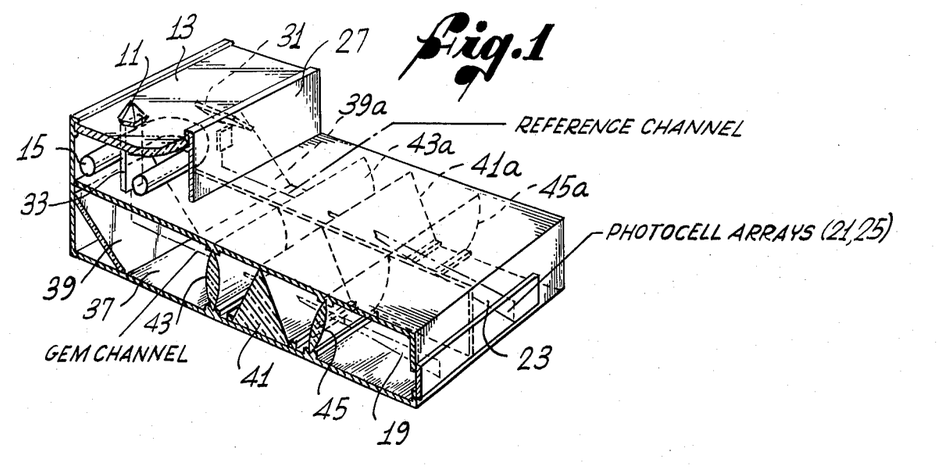
FIG. 1 is a perspective view of apparatus in accordance with the preferred embodiment of the present invention, for use in providing measurements of the spectral transmission characteristics of gems, particularly diamonds.
Figure 2:
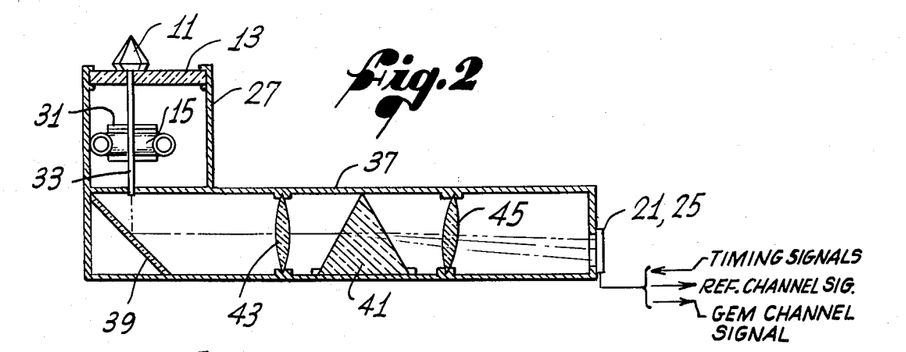
FIG. 2 is a sectional elevational view of the apparatus of FIG. 1, showing the optical path followed by light transmitted through the gem being examined.

With reference now to the drawings, and particularly to FIGS. 1 and 2, there is shown an apparatus for use in determining the spectral transmission characteristics of gems, particularly diamonds. A diamond 11 to be examined is placed on a diffuser plate 13 on the top side of the apparatus, with the table of the diamond facing downwardly, and polychromatic light from a U-shaped flash lamp 15 is directed at the diamond. The light enters the diamond through its facets, if reflected internally, and is then transmitted out through the table. The emergent light beam 19, which has a spectral distribution differing from that of the light emitted by the lamp in accordance with the spectral transmission characteristics of the diamond, is transmitted along a gem channel optical path to a gem channel array of photodiodes 21, where the spectral distribution of the transmitted light is determined.

In accordance with the present invention, the apparatus further functions to simultaneously direct a reference beam of light 23 along a reference channel optical path from the flash lamp 15 to a reference channel array of photodiodes 25, where its spectral distribution is determined. The respective measurements produced in the two photodiode arrays 21 and 25 are then compared with each other in a prescribed fashion by special monitoring circuitry (FIG. 3), to provide accurate measurements of the actual spectral transmission characteristics of the diamond 11. Since these measurements are obtained by monitoring the respective gem channel and reference channel light beams 19 and 23 simultaneously, undesired effects arising from variations in time of the spectral distribution of the light emitted by the lamp are avoided.

The apparatus further functions to compare these transmission measurements with each other in a prescribed fashion, to grade the diamond 11 according to conventional Gemological Institute of America (GIA) grading standards, including color grade, fluorescence, brown character, yellow character, and brilliance. The grade determinations provided by the apparatus correlate well with those that would be obtained empirically by skilled observers under ideal conditions, and are provided relatively quickly and in a highly reliable and repeatable fashion.

More particularly, the U-shaped flash lamp 15 is positioned in a horizontal orientation in an upper, lamp housing 27, and the diffuser plate 13 forms the upper wall of this housing. The diamond 11 is positioned on the diffuser plate with its table located over an aperture 29 formed therein. Polychromatic light from the lamp impinges on the plate, causing it to act as a secondary source of light, and this light then enters the diamond through its facets, is reflected internally and then directed out through the table into the aperture to form the gem channel beam of light 19. Additionally, a reference beam mirror 31 is positioned within the lamp housing, adjacent the closed end of the U-shaped flash lamp, and this mirror is oriented to direct light from the lamp downwardly to form the reference channel beam of light 23.

The gem channel and reference channel light beams 19 and 23 are transmitted through light tubes 33 and 35, respectively, which extend through the upper, lamp housing 27 to a lower housing 37. The two light tubes have rectangular cross-sections, with internal demensions of about five millimeters by 0.1 millimeters, and, additionally, the tubes are opaque, to prevent extraneous light from entering them directly from the lamp 15.

The gem channel optical path is formed by the light tube 33 which is located in the lamp housing 27, and by a mirror 39, a prism 41, and a pair of linear, convex lenses 43 and 45, which are located in the lower housing 37. The gem channel light beam 19 enters the lower housing via the light tube and is then reflected by the mirror and transmitted through the prism and the two lenses to the gem channel photodiode array 21. The prism functions to disperse the beam according to its component wavelengths bands, and the lenses function to focus each band onto a separate photodiode in the array. Each photodiode in the array therefore produces an electrical signal representative of the intensity of light in a prescribed wavelength band.

In similar fashion, the reference channel optical path is formed by the light tube 35, located in the lamp housing 27, and by a mirror 39a, a prism 41a, and a pair of linear, convex lenses 43a and 45a, located in the lower housing 37. These elements are substantially identical in structure and function to the corresponding elements that form the gem channel optical path. The reference channel light beam 23 thus is dispersed according to its component wavelength bands and focused onto the reference channel photodiode array 25. Each photodiode then produces an electrical signal representative of the intensity of light in a prescribed wavelength band, which is substantially the same band as that for the corresponding photodiode of the gem channel photodiode array 21. Additionally, a separation panel 46 is positioned within the lower housing, to separate the elements that form the respective gem channel and reference channel optical paths and thereby provide isolation for the two light beams.

The U-shaped flash lamp 15 preferably emits light that is substantially white, having a significant intensity over a wavelength range extending from about 350 nm to 700 nm. The flash lamp is pulsed for a relatively short duration, such as 100 microseconds, long enough only to permit suitable detection by the photodiodes in the two arrays 21 and 25. This reduces a build-up of heat that otherwise could adversely affect operation of the photodiodes.

The reference beam mirror 31 and the mirrors 39 and 39a are preferably backed with silver, so that they will have a negligible effect on the spectral distribution of the two beams of light 19 and 23. Further, it will be appreciated that the gem channel and reference channel optical paths are essentially identical, so the spectral distributions of the two light beams should be affected substantially equally.

Additionally, since the two beams pass through essentially identical prisms 41 and 41a, they should be dispersed substantially equally, and the particular wavelength band detected by each photodiode in the gem channel array 21 should correspond to that detected by the corresponding photodiode in the reference channel array 25. Accordingly, a comparison of the electrical signal produced by each photocell in the gem channel array with the electrical signal produced by the corresponding photodiode in the reference channel array provides an accurate indication of the actual transmission of the diamond 11 in that particular wavelength band.

In the preferred embodiment, the gem channel and reference channel photodiode arrays 21 and 25 are linear arrays of contiguous photodiodes, such as an RL 512G solid state line scanner produced by Reticon Corporation of Sunnyvale, Calif. These devices are linear arrays of 512 photodiodes, arranged on 25 micron centers. The electrical signals produced by the successive photodiodes in each device can be read out in a serial fashion, to produce an analog waveform that varies in accordance with the spectral distribution of the corresponding light beam. Each device is positioned such that light having a wavelength of about 350 nm impinges on the first photodiode and light having a wavelength of about 700 nm impinges on the 512th photodiode.

Figure 3:
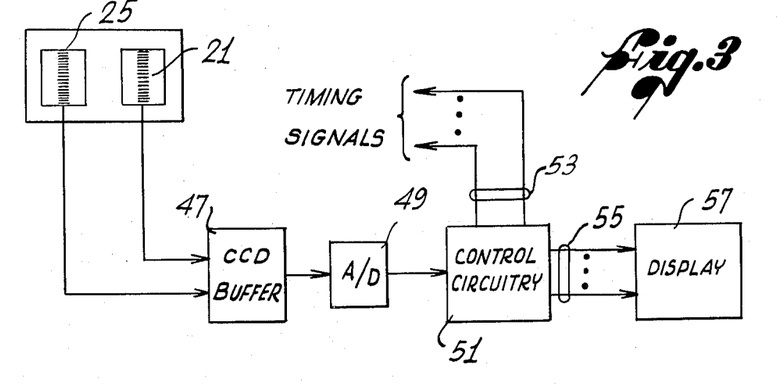
FIG. 3 is a simplified block diagram of circuitry utilized in processing the light intensity measurements produced by the apparatus of FIG. 1.

As shown in FIG. 3, the apparatus further includes circuitry for suitably processing the plurality of light intensity measurements produced by the two photodiode arrays 21 and 25, to produce measures of the actual spectral transmission characteristics of the diamond 11. The circuitry includes a CCD buffer 47 into which the plurality of measurements from the two arrays are initially clocked, an A/D converter 49 for successively converting the plurality of measurements into a digital format, and control circuitry 51 for suitably processing the succession of digital words to produce the various measures of spectral transmission.

The control circuitry 51 includes means for outputting conventional timing signals on lines 53 for coupling to the flash lamp 15, the photodiode arrays 21 and 25, the CCD buffer 47, and the A/D converter 49 to appropriately control their operations. These timing signals function to synchronize pulsing of the lamp with the clocking of the light intensity measurements into the CCD buffer, and the conversion of these measurements into digital words by the A/D converter. Additionally, the control circuitry includes conventional digital storage devices for storing the successive digital words supplied by the A/D converter, and a conventional microprocessor for processing the stored data in a prescribed fashion, as discussed below.

After the successive light intensity measurements from the respective gem channel and reference channel photodiode arrays 21 and 25 have been digitized and entered into the control circuitry 51 for storage, the circuitry functions in a conventional manner to compute the ratio of each corresponding pair of measurements. This yields 512 successive quotients indicative of the difference in intensities of the gem channel and reference channel beams of light, for prescribed wavelength bands extending from about 350 nm to 700 nm.

Thereafter, the control circuitry 51 functions to adjust each of the 512 quotients to account for differences in the sensitivities of the various photodiodes and for differences in the spectral characteristics of the gem channel and reference channel optical paths. Specifically,, each quotient is multiplied by a calibration factor determined for the corresponding photodiode pair during an initial calibration procedure, when the apparatus is initially constructed. These calibration factors are stored in a read-only-memory in the control circuitry.

In the initial calibration procedure for determining the 512 calibration factors, a silver-backed mirror (not shown) is placed over the gem channel aperture 29 in the diffuser plate 13 (where the diamond 11 is normally positioned), so that polychromatic light from the flash lamp 15 is transmitted along both the gem channel and reference channel optical paths to the respective photodiode arrays 21 and 25. Differences in the spectral sensitivities of the two channels and of the individual photodiodes in the two arrays will therefore be reflected in the electrical signals output by the two arrays. Each calibration factor is then determined by computing the ratio of the electrical signals produced by the corresponding photodiodes of the reference channel and gem channel arrays.

Adjustment of the 512 quotients in accordance with the stored calibration factors for each photodiode pair thus yields 512 normalized transmission measurements indicative of the actual transmission of the diamond 11 for 512 prescribed wavelength bands. Each normalized measurement corresponds to a separate wavelength band in the region extending from 350 nm to 700 nm and each measurement has a maximum value of 1.0, indicating that the diamond has a transmission of substantially 100 percent in the corresponding wavelength band, and a minimum value of 0, indicating that the diamond has a transmission of substantially 0 in the corresponding wavelength band.

The control circuitry 51 is further adapted to suitably process the 512 normalized transmission measurements to grade the diamond 11 in a manner corresponding generally to conventional GIA grading standards. Specifically, the diamond is graded according to its color grade, fluorescence, brown character, yellow character, and brilliance. The determinations are made by averaging the normalized transmission measurements for prescribed groups of wavelength bands and by then comparing such average values with the average values for other prescribed groups of wavelength bands.

Figure 4:
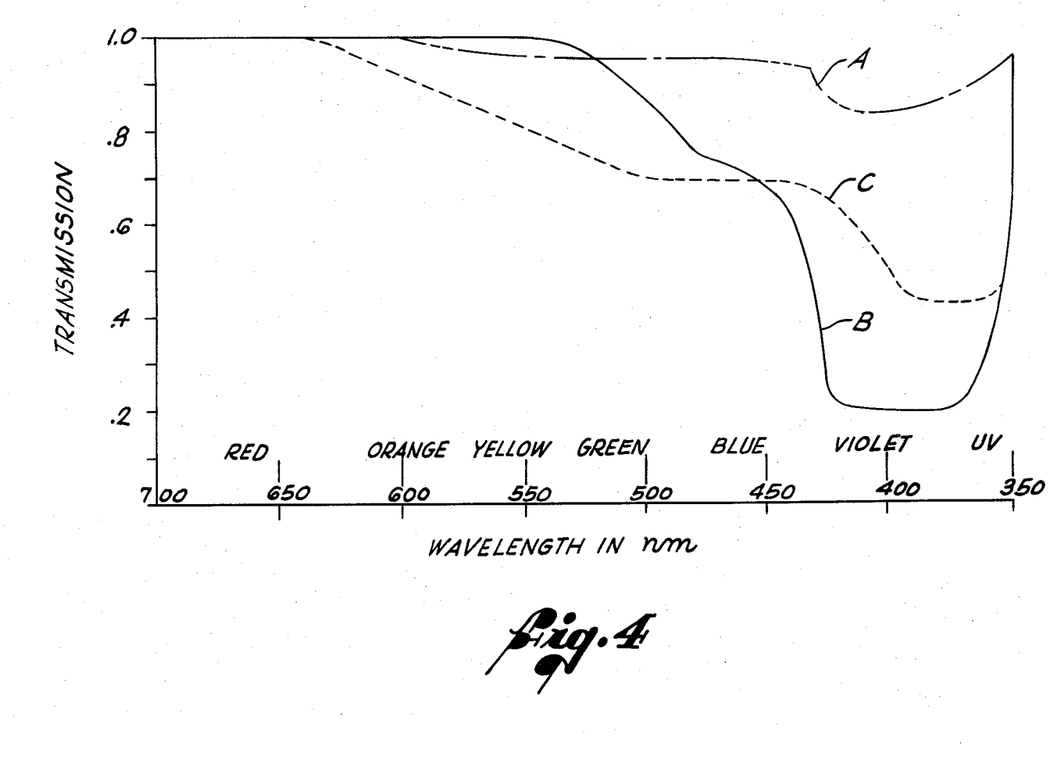
FIG. 4 is a graphic representation of the spectral transmission characteristics of three representative diamonds having prescribed color characteristics.

By way of example, FIG. 4 is a graph of the spectral transmission characteristics of three representative diamonds having prescribed color characteristics. The graph includes along its abscissa an identification of the colors represented generally by the various wavelengths of the light. The curve indicated by the reference letter A represents the transmission spectrum of a diamond of high quality, curve B represents the transmission spectrum of a fancy yellow diamond, and curve C represents the transmission spectrum of a brown diamond.

The high quality diamond (curve A) is characterized by a high level of transmission across the entire spectrum, with a slight decrease in transmission in the near ultraviolet (UV) range, starting at about 420 nm. The fancy yellow diamond (curve B) is characterized by a significant absorption centered at about 500 nm, and additionally a precipitous absorption in the near UV range. Lastly, the brown diamond, (curve C), which is the lowest quality diamond of the three illustrated, is characterized by a significant absorption over a broad range of the visible spectrum.

The magnitude of the transmission in the near UV range generally correlates well with the basic color grading of diamonds. This is evidenced by the fact that the fancy yellow diamond (curve B) transmits considerably less light in the near UV range than does the high quality diamond (curve A). This general correlation between color grading and transmission in the near UV range has led many workers in the field to attempt to grade the color of diamonds by measuring the transmission of monochromatic light in the near UV range, for example, at about 415 nm. This system of grading, however, can easily produce misleading results since a brown diamond (curve C) has a higher transmission in the near UV range, but is of a lower quality.

In order to avoid such misleading results, it is believed necessary to measure the transmission characteristics of a diamond over a broad range of the spectrum and to compare these measurements with one another in a prescribed fashion to arrive to an accurate and reliable conclusion as to the true quality of the diamond. The present invention achieves this result by measuring the transmission of a diamond in numerous wavelength bands and by then comparing the measurements in a manner described below.

Specifically, the color grade of the diamond 11 is determined by comparing the average value of the normalized transmission measurements corresponding to a near ultra-violet wavelength range, preferably 350 nm to 400 nm, with the average value of the normalized transmission measurements a reference red-orange wavelength region, i.e., preferably about 650 nanometers to 700 nanometers. The red-orange transmission measurements are preferably used as a reference, since the transmission of most diamonds is close to 100% in this region. By dividing the average ultra-violet measurement by the average red-orange measurement, a numerical color grade value between 0 and 1.0 is derived, with higher numbers representing higher quality stones.

By similarly testing a set of industry standard diamonds of known quality, containing no fluorescence or brownness, and being identified by the standard letter grading from D to R of the GIA scale, appropriate numerical thresholds for each letter grading can be ascertained. By then comparing the numerical color grade value determined for the diamond 11 being examined to the various thresholds, an appropriate letter grade can be assigned to the diamond.

The control circuitry 51 (FIG. 3) is further adapted to produce suitable electrical signals representative of the specific color grade determined for the diamond 11 being examined, either in the aforementioned numerical format or the letter grade format. These signals are coupled over lines 55 to a suitable visual display 57.

The fluorescence of the diamond 11 is determined by comparing the numerical coloring grade for the diamond with a similar grade that is determined by comparing the average value of the normalized transmission measurements for the blue-violet wavelength range with the average value in the reference, red-orange range. Preferably, the blue-violet range extends from about 400 nm to about 500 nm and the red-orange range extends from about 650 nm to about 700 nm. If the blue-violet grading is substantially equal to the ultra-violet grading (i.e., the color grade determined above), no presence of fluorescence is indicated. On the other hand, a blue-violet grading significantly higher than the ultra-violet grading is an indication that the diamond is emitting its own light in the blue-violet range and is therefore fluorescent. The degree of fluorescence is roughly proportional to the difference between the blue-violet and ultra-violet gradings. A suitable electrical signal indicative of this difference is coupled over lines 55 to the display 57, to provide a visual indication of the fluorescence of the diamond 11.

The brown character of the diamond 11 is determined by comparing the average value of the normalized transmission measurements corresponding to the green-orange wavelength region, preferably extending from about 525 nm to about 625 nm, with the reference transmission average in the red-orange range, preferably about 650 nm to 700 nm. As discussed above, a brown diamond is characterized by a significant absorption over a broad range of the visible spectrum, extending from about 350 nm to about 625 nm. Consequently, a diamond transmitting substantially less light in the wavelength region extending from about 525 nm to 625 nm than in the region of 650 nm to 750 nm will exhibit the characteristic of brownness, with the degree of brownness generally proportional to the difference between these transmission values. An electrical signal indicative of this difference is coupled over lines 55 from the control circuitry 51 to the display 57, to provide a visible indication of the brownness of the diamond.

Alternatively, the brownness of the diamond 11 can be related to that of diamonds previously graded empirically by skilled observers in accordance with GIA grading standards. This can be accomplished, for example, by computing the brownness ratio for a diamond previously assigned a grade of "very brown", and by then comparing this ratio to the ratio computed for the diamond 11 being examined. A brownness number for the diamond can then be determined by dividing the latter ratio by the former ratio and by then multiplying the resultant quotient by 100. An electrical signal indicative of this brownness number can then be output over lines 55 from the control circuitry 51 to the display 57.

As shown in FIG. 4, a yellow diamond (curve B) is characterized by a substantially uniform transmission for relatively long wavelengths, with a broad absorption range for wavelengths shorter than about 550 nm. Accordingly, the yellow character of the diamond 11 is determined by comparing its transmission in the blue-green wavelength region to its transmission in a reference wavelength region, preferably the red-orange region. Thus, in the preferred embodiment, the average value of the normalized transmission measurements corresponding to wavelength bands between about 450 nm and 550 nm is divided by the average value of measurements corresponding to bands between about 650 mn and 700 nm. This provides a numerical grade indicative of the yellow character of the diamond, and a corresponding electrical signal is output over lines 55 to the display 57.

Alternatively, the yellow character of the diamond 11 can be related to that of diamonds previously graded empirically by skilled observers in accordance with GIA grading standards. This can be accomplished, for example, by computing the yellowness ratio for a diamond previously assigned a grade of "very yellow", and by then comparing this ratio to the ratio computed for the diamond 11 being examined. A yellowness number for the diamond can then be determined by dividing this latter ratio by the former ratio, and by then multiplying the resultant quotient by 100. An electrical signal indicative of this yellowness number can then be output over lines 55 from the control circuitry 51 to the display 57.

Finally, the brilliance of the diamond 11 being examined can be determined by summing together all of the 512 separate normalized transmission measures, and by then dividing this sum by a measure of the average diameter of the diamond. This average diameter measurement can be conveniently input to the control circuitry 51 by means of a keyboard (not shown). An electrical signal indicative of the resultant measure of brilliance is supplied over line 55 from the control circuitry to the display 57.

It will be appreciated from the foregoing description that the present invention provides an effective apparatus for producing accurate measurements indicative of the spectral transmission characteristics of gems. The measurements are not affected by variations in the spectral distribution of the light being used or by differences in the sensitivities in the devices used to measure light intensity. Additionally, it will be appreciated that the present invention provides accurate and reliable methods for grading a diamond in accordance with its color grade, fluorescence, brown character, yellow character, and brilliance, in a manner corresponding well with empirical testing by skilled observers under ideal conditions.

While a particular form of the invention has been illustrated and described, it will be understood by one of ordinary skill in the art that various modifications can be made, without departing from the spirit and scope of the invention. Accordingly, it is not intended that the invention be limited, except as by the appended claims.

I claim:

1. Apparatus for measuring the spectral transmission characteristics of a gem, comprising:
   a source of polychromatic light;
   means for supporting the gem in a position to receive a portion of the light from said light source, said light being transmitted by the gem in accordance with the spectral transmission characteristics of the gem;
   first and second, corresponding arrays of phototransducers;
   optical means for defining a gem channel optical path and a reference channel optical path, said optical means including
      first means for collecting light transmitted by the gem to form a gem channel beam of light for transmission along the gem channel optical path to said first array of phototransducers,
      second means, operable simultaneously with said first means, for collecting a portion of the light from said light source to form a reference channel beam of light for transmission along the reference channel optical path to said second array of phototransducers, and
      means for separating each of the gem channel and reference channel beams of light into a plurality of separate wavelength bands, and for directing the light in each wavelength band at a separate phototransducer in the corresponding array of phototransducers, whereby a plurality of corresponding light intensity measurements are produced by each array; and
   means for comparing each light intensity measurement from said first array with the corresponding light intensity measurement from said second array, to produce a plurality of normalized measurements representative of the spectral transmission characteristics of the gem.

2. Apparatus as defined in claim 1, wherein said source of light comprises a flash lamp that is pulsed for a duration sufficient to permit the phototransducers in said first and second arrays to properly detect the intensity of the light impinging thereon, whereby an excessive build-up of heat from the source of light is avoided.

3. Apparatus as defined in claim 1, wherein:
   said means for supporting comprises a diffuser plate having means defining an aperture therein; and
   said gem is positioned over the aperture in said diffuser plate, whereby the light emerging from the gem is directed through the aperture to form the gem channel beam of light.

4. Apparatus as defined in claim 1, wherein the elements of said optical means for defining the respective gem channel and reference channel optical paths are substantially identical in structure and function.

5. Apparatus as defined in claim 1, wherein said means for separating of said optical means includes prism means for dispersing the gem channel and reference channel beams of light into their component wavelengths.

6. Apparatus as defined in claim 1, wherein each of said first and second arrays of phototransducers comprises a linear array of contiguous photodiodes.

7. Apparatus as defined in claim 1, wherein said means for comparing includes:
   means for dividing each light intensity measurement from said first array of phototransducers by the corresponding light intensity measurement from said second array of phototransducers, to produce a plurality of quotients indicative of the difference in the intensities of the gem channel and reference channel beams of light for each of said wavelength bands; and
   means for adjusting each quotient in accordance with a prescribed calibration factor indicative of the difference in the sensitivities of the corresponding phototransducers, to produce the plurality of normalized measurements representative of the spectral transmission characteristics of the gem.

8. Apparatus for measuring the spectral transmission characteristics of a gem, comprising:
   a source of polychromatic light;
   means for directing light from said light source at the gem, said light being transmitted by the gem in accordance with its spectral transmission characteristics;
   first measuring means for measuring the spectral distribution of the light transmitted by the gem;
   second measuring means, operable simultaneously with said first measuring means, for measuring the spectral distribution of light from said light source; and
   means for comparing the measurements produced by said first and second measuring means, to produce normalized measurements representative of the spectral transmission characteristics of the gem.

9. Apparatus as defined in claim 8, wherein said source of light comprises a flash lamp that is pulsed for a duration sufficient to permit said first and second measuring means to accurately measure the spectral distribution of the corresponding light.

10. Apparatus as defined in claim 8, wherein each of said first and second measuring means includes a linear array of contiguous phototransducers, each phototransducer producing a measurement of the intensity of light in a prescribed, unique band of wavelengths.

11. Apparatus as defined in claim 10, wherein said means for comparing includes:
means for dividing each light intensity measurement produced by said first measuring means by the corresponding light intensity measurement produced by said second measuring means, to produce a plurality of quotients indicative of the difference in the intensities of the light transmitted by the gem and the light emitted by the light source for each of said wavelength bands; and
means for adjusting each quotient in accordance with a prescribed calibration factor indicative of the difference in the sensitivities of the corresponding phototransducers, to produce a plurality of normalized measurements representative of the spectral transmission characteristics of the gem.

12. A method for determining the spectral transmission characteristics of a gem, comprising the steps of:
directing polychromatic light at the gem from a light source, said light being transmitted by the gem in accordance with its spectral transmission characteristics to form a gem channel beam of light;
separating the gem channel beam of light into a plurality of separate wavelength bands, and directing the light in each band at a separate phototransducer, thereby producing a plurality of gem channel measurements indicative of the spectral distribution of the light transmitted by the gem;
forming a reference channel beam of light from polychromatic light emitted by the light source;
separating the reference channel beam of light into a plurality of separate wavelength bands, and directing the light in each band at a separate phototransducer, thereby producing a plurality of reference channel measurements indicative of the spectral distribution of the light emitted by the light source; and
comparing each of said plurality of gem channel measurements with the corresponding one of said plurality of reference channel measurements, to produce a plurality of normalized measurements indicative of the spectral transmission characteristics of the gem.

13. A method as defined in claim 12, wherein said step of comparing includes the steps of:
dividing each of said plurality of gem channel measurements by the corresponding one of said plurality of reference channel measurements, to produce a quotient indicative of the difference in the intensities of the light transmitted by the gem and the light emitted by the light source, for each of said wavelength bands; and
adjusting each quotient in accordance with a prescribed calibration factor indicative of the difference in the sensitivities of the corresponding phototransducers, to produce the plurality of normalized measurements representative of the spectral transmission characteristics of the gem.

14. A method as defined in claim 12, wherein:
said gem is a diamond; and
said method further includes a step of comparing the normalized measurements corresponding to wavelength bands in the near ultra-violet region with the normalized measurements corresponding to wavelength bands in the red-orange region, to produce a measure of the color grade of the diamond.

15. A method as defined in claim 14, wherein said step of comparing normalized measurements includes the steps of:
determining the average value of the normalized measurements for the near ultra-violet region;
determining the average value of the normalized measurements for the red-orange region; and
computing the ratio of said average values, to produce the measure of the color grade of the diamond.

16. A method as defined in claim 14, wherein:
said near ultra-violet region includes wavelength bands located between about 350 nanometers and about 400 nanometers; and
said red-orange region includes wavelength bands located between about 650 nanometers and about 700 nanometers.

17. A method as defined in claim 12, wherein:
said gem is a diamond; and
said method further includes a step of comparing the normalized measurements corresponding to wavelength bands in the blue-violet region with the normalized measurements corresponding to wavelength bands in the near ultra-violet region, to produce a measure of the fluorescence of the diamond.

18. A method as defined in claim 17, wherein said step of comparing normalized measurements includes the steps of:
determining the average value of the normalized measurements for the blue-violet region;
determining the average value of the normalized measurements for the near ultra-violet region;
determining the average value of the normalized measurements for the red-orange region;
computing the ratio of the average value of the blue-violet region to the average value for the red-orange region;
computing the ratio of the average value for the near ultra-violet region to the average value for the red-orange region; and
comparing the two ratios, to produce the measure of the fluorescence of the diamond.

19. A method as defined in claim 17, wherein:
said blue-violet region includes wavelength bands located between about 400 nanometers and about 500 nanometers; and
said near ultra-violet region includes wavelength bands located between about 350 nanometers and about 400 nanometers.

20. A method as defined in claim 12, wherein:
said gem is a diamond; and
said method further includes a step of comparing the normalized measurements corresponding to wavelength bands in the green-orange region with the normalized measurements corresponding to wavelength bands in the red-orange region, to produce a measure of the brown character of the diamond.

21. A method as defined in claim 20, wherein said step of comparing normalized measurements includes the steps of:

determining the average value of the normalized measurements for the green-orange region;

determining the average value of the normalized measurements for the red-orange region; and computing the ratio of said average values, to produce the measure of brown character of the gem.

22. A method as defined in claim 20, wherein:

said green-orange region includes wavelength bands located between about 525 nanometers and 625 nanometers; and said red-orange region includes wavelength bands located between about 650 nanometers and 700 nanometers.

23. A method as defined in claim 12, wherein:

said gem is a diamond; and said method further includes a step of comparing the normalized measurements corresponding to wavelength bands in the blue-green region with the normalized measurements corresponding to wavelength bands in the red-orange region, to produce a measure of the yellow character of the diamond.

24. A method as defined in claim 23, wherein said step of comparing normalized measurements includes the steps of:

determining the average value of the normalized measurements for the blue-green region;

determining the average value of the normalized measurements for the red-orange region; and computing the ratio of said average values, to produce the measure of yellow character of the gem.

25. A method as defined in claim 23, wherein:

said blue-green region includes wavelength bands located between about 450 nanometers and 550 nanometers; and said red-orange region includes wavelength bands located between about 650 nanometers and 700 nanometers.

26. A method as defined in claim 12, and further including the steps of:

summing together the plurality of normalized measurements to produce a sum signal; and dividing the sum signal by a measure of the average diameter of the gem, to produce a measure of the brilliance of the gem.

27. A method as defined in claim 26, wherein said plurality of wavelength bands includes wavelengths between about 350 nanometers and about 700 nanometers.

* * * * *